US011406650B2

(12) United States Patent
Sakwinska et al.

(10) Patent No.: US 11,406,650 B2
(45) Date of Patent: Aug. 9, 2022

(54) PREBIOTICS FOR REDUCING THE RISK OF OBESITY LATER IN LIFE

(71) Applicant: NESTEC S.A., Vevey (CH)

(72) Inventors: Olga Sakwinska, Lausanne (CH); Bernard Berger, Maracon (CH); Irma Silva Zolezzi, Carrouge (CH); Joanna Holbrook, Singapore (SG)

(73) Assignee: Societe des Produits Nestle S.A., Vevey (CH)

( * ) Notice: Subject to any disclaimer, the term of this patent is extended or adjusted under 35 U.S.C. 154(b) by 156 days.

(21) Appl. No.: 15/504,916

(22) PCT Filed: Aug. 4, 2015

(86) PCT No.: PCT/EP2015/067885
§ 371 (c)(1),
(2) Date: Feb. 17, 2017

(87) PCT Pub. No.: WO2016/026684
PCT Pub. Date: Feb. 25, 2016

(65) Prior Publication Data
US 2017/0273997 A1 Sep. 28, 2017

(30) Foreign Application Priority Data
Aug. 18, 2014 (EP) .................................. 14181275

(51) Int. Cl.
| A61K 31/702 | (2006.01) |
| A23L 5/00 | (2016.01) |
| A23L 33/125 | (2016.01) |
| A23L 29/30 | (2016.01) |
| A23L 33/00 | (2016.01) |
| A23L 33/135 | (2016.01) |
| A23L 33/21 | (2016.01) |
| A23L 33/19 | (2016.01) |
| A61K 35/745 | (2015.01) |

(52) U.S. Cl.
CPC .............. *A61K 31/702* (2013.01); *A23L 5/00* (2016.08); *A23L 29/30* (2016.08); *A23L 33/125* (2016.08); *A23L 33/135* (2016.08); *A23L 33/19* (2016.08); *A23L 33/21* (2016.08); *A23L 33/30* (2016.08); *A23L 33/40* (2016.08); *A61K 35/745* (2013.01); *A23V 2002/00* (2013.01)

(58) Field of Classification Search
CPC ..... A61K 31/702; A61K 35/745; A23L 33/21; A23L 33/19; A23L 33/30; A23L 5/00; A23L 33/125; A23L 29/30; A23L 33/40; A23L 33/135; A23L 33/10; A23V 2002/00; A61P 3/04
See application file for complete search history.

(56) References Cited

U.S. PATENT DOCUMENTS

2003/0129278 A1 7/2003 Stahl et al.
2009/0220639 A1* 9/2009 Schmitt ................... A23L 33/40
426/2

FOREIGN PATENT DOCUMENTS

| EP | 2030623 | 3/2009 |
| EP | 2143341 | 1/2010 |
| WO | 0160346 | 8/2001 |
| WO | 2007090894 A1 | 8/2007 |
| WO | 2011093907 A1 | 8/2011 |
| WO | 2011096808 | 8/2011 |
| WO | 2015092047 A2 | 6/2015 |

OTHER PUBLICATIONS

Veereman, J. Nutr. 137: 2585S-2589S, 2007.*
Donovan et al (Jan. 6, 2010) (https://www.meadjohnson.com/pediatrics/us-en/sites/hcp-usa/files/LB2329-Prebiotics.pdf).*
Puccio et al., Nutrition 23 (2007) 1-8.*
Veereman et al., J. Nutr. 137: 2585S-2589S, 2007.*
Zivkovic et al., Adv Nutr. May 2011;2(3):284-9.*
Favier et al. Molecular Monitoring of Succession of Bacterial Communities in Human Neonates. Appl. Environ. Microbiol. 2002;68(1):219-226.*
Gillman, "The first months of life: a critical period for development of obesity", The American Journal of Clinical Nutrition, Jun. 2008, vol. 87, No. 6, pp. 1587-1589, XP9505778.
Sun et al., "Childhood Obesity Predicts Adult Metabolic Syndrome: The Fels Longitudinal Study", The Journal of Pediatrics, Feb. 2008, vol. 152, No. 2, pp. 191-200.e1, XP029610893.
Yu et al. "Trametes versicolor Extract Modifies Human Fecal Microbiota Composition In vitro" Plant Foods Hum Nutr, 2013, vol. 68, pp. 107-112.
Marcobal et al., "Consumption of Human Milk Oligosaccharides by Gut-related Microbes", J. Agric. Food Chem., vol. 58, Issue No. 9, May 12, 2010, pp. 5334-5340.
Chinese Office Action for Chinese Appl No. 201580043982.5 dated May 5, 2022.

* cited by examiner

Primary Examiner — Lynn Y Fan
(74) Attorney, Agent, or Firm — K&L Gates LLP

(57) ABSTRACT

The invention proposes a nutritional composition comprising selected oligosaccharides that reduces the abundance of *Streptococcus* bacteria in the gut of infants or young mammals. The infants are preferably infants in needs presenting a relatively high count of *Streptococcus*. Ultimately the reduction of *streptococcus* and the related microbiota balance affects and lowers the risk of adiposity or obesity later in life.

17 Claims, 5 Drawing Sheets

Streptococcus relative abundance at 6 months

Spearman- Rank- Correlation = 0.197
Pearson R =0.352
R-squared =0.124
p-value=0.0176

Reduction of Streptococcus abundance in infants receiving oligosaccharides.

Reduction of Streptococcus abundance in mice receiving oligosaccharides.

No reduction of Streptococcus in adult volunteers receiving FOS-inulin and probiotic LPR.

Reduction of Streptococcus abundance in infants receiving formula with BMOS oligosaccharides (EXP2) as compared to control formula (EXP1).

PREBIOTICS FOR REDUCING THE RISK OF OBESITY LATER IN LIFE

CROSS REFERENCE TO RELATED APPLICATIONS

The present application is a National Stage of International Application No. PCT/EP2015/067885, filed on Aug. 4, 2015, which claims priority to European Patent Application No. 14181275.0, filed Aug. 18, 2014, the entire contents of which are being incorporated herein by reference.

FIELD OF THE INVENTION

The present invention relates to the use of specific oligosaccharides for modulating the gut microbiota, more specifically reducing the count of *Streptococcus* in the gut in a young subject, preferably an infant. More particularly, the present invention relates to such use of oligosaccharides probiotics for ultimately reducing the risk of obesity later in life.

BACKGROUND OF THE INVENTION

The prevalence of obesity has grown in an alarming rate in the past 20 years. Based on an estimate in 2004, in the US alone, 66.3% of adults are either overweight or obese, and 32.2% of adults are classified as obese (Cynthia L. Ogden et al., JAMA 2006 Apr. 5; 295:1549-1555). Both genetic and environmental factors have been shown to cause positive energy balance and obesity. Obesity by itself is only a part of problems. Many other chronic diseases such as type 2 diabetes, certain cancers and cardiovascular diseases are common co-morbidities of obesity. Collectively, all the obesity associated medical issues put a tremendous amounts of pressure on health care systems in many countries.

Drug treatments for obesity are available but not very effective and with undesirable side-effects. Still more drugs are under development to improve the safety, efficacy of the medications and convenience to use them by patients. To date, all anti-obesity treatments are designed to alter the internal metabolism of patients. Most of these drugs are required to be absorbed and delivered to target organs through blood stream for their efficacy. Safety concerns of such a treatment strategy cannot be ignored.

Novel treatment strategies of obesity and type 2 diabetes focussing on targets outside of human tissues is greatly desirable because the active agents are not required to enter our body, and the safety of the treatments can be improved significantly.

Recent research has shown that gut bacteria play a role in the development of obesity and related metabolic disorders such as diabetes (Kristina Harris, et al., Journal of Obesity 2012; 2012:879151; doi:10.1155/2012/879151). Human beings are super-organisms with a body composed of millions of human cells while many more bacteria live, e.g., in the colon. It has been estimated that more than $10^{13}$ to $10^{14}$ bacteria are alive in a healthy human intestine. Intestinal bacteria can be separated into 2 major divisions, *Firmicutes and Bacteriodetes* (Steven R. Gill, et al., Science 2006 Jun. 2; 312:1355-1359; Peter J. Turnbaugh, et al., Nature 2006 Dec. 21; 444:1027-131). Together, they represent at least 90% of total bacterial population in the gut. The presence of the gut bacteria is a part of normal human physiology and is important for the development of gut functions (Hooper L V et al., Science. 2001 Feb. 2; 291(5505):881-4; Stappenbeck T S, et al., Proc Natl Acad Sci USA. 2002 Nov. 26; 99(24):15451-5), maturation of the immune system (Mazmanian S K, et al., Cell. 2005 Jul. 15; 122(1):107-18), harvesting energy from dietary carbohydrates (Peter J. Turnbaugh, et al., Nature 2006 Dec. 21; 444:1027-131), harvesting essential vitamins (Backhed F, et al., Science. 2005 Mar. 25; 307(5717):1915-20) and metabolizing environmental chemicals in the gut (Nicholson J K, et al., Nat Rev Microbiol. 2005 May; 3(5):431-8). Recent studies further suggested that gut bacteria may be involved in fat storage (Backhed F, et al., Proc Natl Acad Sci USA. 2004 Nov. 2; 101(44):15718-23).

Infancy, especially the first weeks, 3 months, 6 months or 12 months of life is critical for the establishment of a balanced gut microbiota.

It is know that the modulation of the gut microbiota during infancy can prospectively have a great influence in the future health status of the bodies, in particular the development of obesity later in life.

Such modulation can be achieved by introducing probiotics in the food consumed.

WO 2006/019222 discloses *Lactobacillus rhamnosus* strain PL60 KCCM-10654P with a body-fat reducing activity that overproduces t10c12-octadecadienoic acid.

U.S. Pat. No. 7,001,756 and CN1670183 provide an isolated microorganism strain *Lactobacillus rhamnosus* GM-020 which is found to be effective in treating obesity.

WO 2009/0218424 describes a composition comprising *Lactobacillus rhamnosus* strain CGMCC 1.3724 or NCC4007 which is useful for supporting weight loss or weight management.

WO 2009/024429 describes a similar composition comprising *Lactobacillus rhamnosus* strain CGMCC 1.3724 or NCC4007 for the use in treating or preventing metabolic disorders. The composition was shown to modify the amount of Proteobacteria in the gut. Optimum results were achieved when the ratio of Proteobacteria to Bacteriodetes was reduced. At the same time, the ratio of Proteobacteria to Firmicutes and/or the ratio of Bacteriodetes to Firmicutes may be increased.

Another approach is to introduce specific nutrients that influence the development of the gut microbiota. Such nutrients can be vitamins, particular proteins, specific fats, or carbohydrates. Some prebiotic oligosaccharides have been described to influence the microbiota of the gut and further have been associated with weight loss or reduction of risk of obesity.

WO2011096808 assigned to Friesland Bands B V, described that sialyl-oligosaccharides in infant formula can enhance the amount of *Bacteroides* ssp. in the gastrointestinal tract and therefore reduce the risk of development of overweight or obesity.

WO2009082214 assigned to N. V. Nutricia, describes that a combination of at least 2 non digestible carbohydrates (prebiotics) can modulate the microbiota in infants, especially decreasing the ratio of Firmicutes/Bacteroidetes and/or *Clostridium*/Bacteroidetes. It is reported that such modulation can act for the prevention of obesity or adiposity.

WO2012024638 assigned to New York university, Dow Global technologies LLC. Nondorf, Laura and Cho Ilseung, describes the down-modulation of Firmicutes and/or Bacteroidetes in the ileal microbiota of mammals. Such modulation can be achieved by the ingestion of saccharides and lead to the treatment or prevention of obesity.

EP2143341A1, assigned to Nestec S A, describes the reduction of obesity later in life by the use of specific oligosaccharide mixtures in nutritional compositions for infants and young children.

However further effectors and modulator of the microbiota still remain to be found.

It is a problem of the present invention to provide additional or alternative means for modulating the gut microbiota in order to modulate the accumulation of fat mass, modulate the adiposity later in life and/or reduce the risk of obesity later in life.

It is a problem of the present invention to provide additional or alternative ways of modulating the gut microbiota in order to modulate the accumulation of fat mass, modulate the adiposity later in life and/or reduce the risk of obesity later in life.

It is a problem of the present invention to provide additional or alternative solutions for re-establishing normal gut microbiota in population affected by suboptimal profile and/or un-balance of gut microbiota. It is a problem to effect such normalization of microbiota in a general or specific manner (specific to certain microorganisms of the gut flora). It is a problem to effect such normalization in a way able to ultimately modulate the accumulation of fat mass, modulate the adiposity later in life and/or reduce the risk of obesity later in life.

It is a problem of the invention to address the above issues in sub-populations particularly affected by general or specific un-balance of the gut microbiota, especially in infant (especially formula-fed infants or sick infants or infants at risk of obesity) or young mammals.

It is a problem of the invention to address the above issues in an effective manner by a nutritional intervention during the first weeks or first months of life.

It is a problem of the invention to ultimately help establishing a normal BMI (body Mass Index) later in life in population at risk of having BMI above normality later in life (e.g. over-weight or obesity).

SUMMARY OF THE INVENTION

The invention relates to a synthetic nutritional composition that comprises prebiotic oligosaccharides for reducing the count of *Streptococcus* bacteria in the gut in formula-fed infants or young mammals such as to reduce the risk of overweight, obesity and/or adiposity later in life. Rapid growth and adiposity rebound in early infancy particularly predispose to risk of obesity in childhood and later in life. The composition of the invention is thought to act in particular by influencing rapid growth and adiposity rebound. The target population of infants is preferably infants at need, i.e. exhibiting an relatively high count of *Streptococcus*. The oligosaccharide of the invention is selected to reduce such count and consequently influence negatively the risk of adiposity or obesity later in life.

DETAILED DESCRIPTION OF THE INVENTION

Definitions

Figure 1:
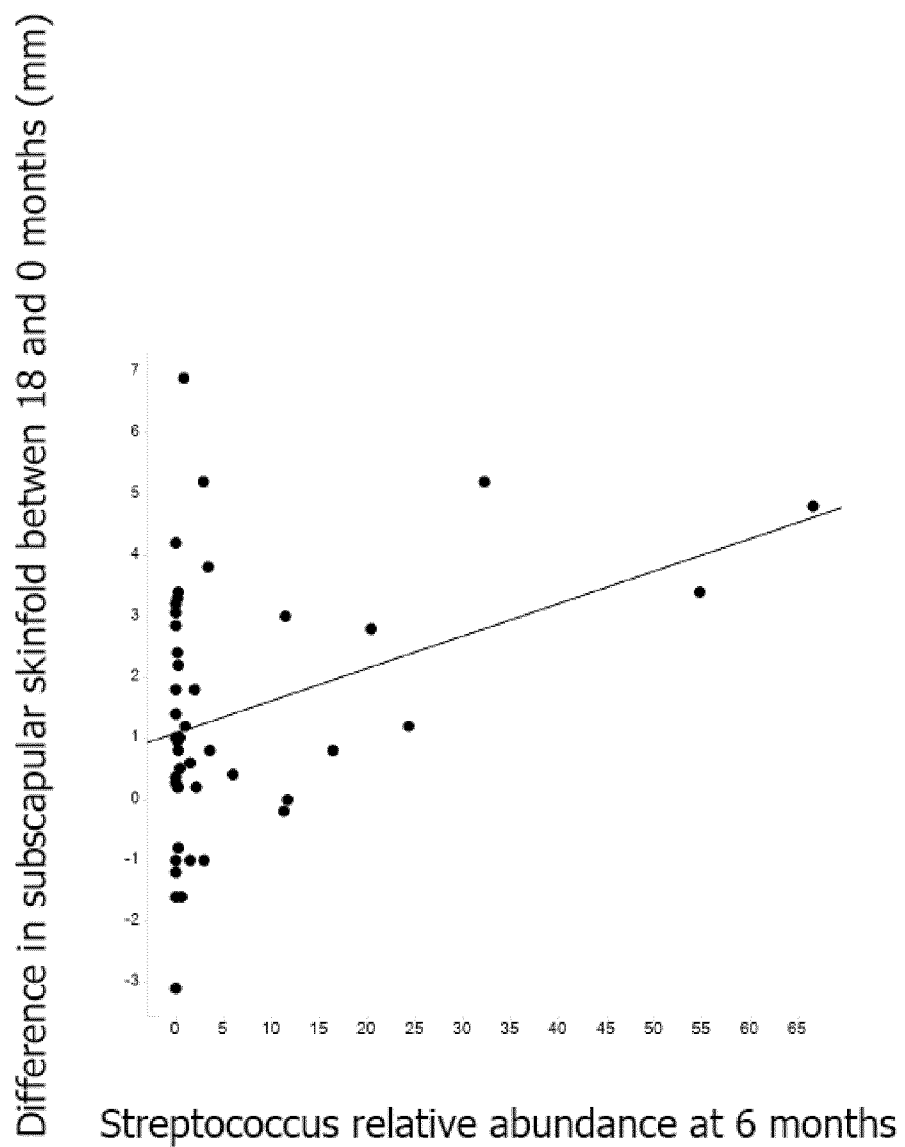
FIG. 1 illustrates the correlation between elevated relative abundance count of *Streptococcus* bacteria in the gut and adiposity gain between birth and 18 months measured in infants.

In this specification, the following terms have the following meanings:

"Infants": according to the Commission Directive 2006/141/EC of 22 Dec. 2006 on infant formulae and follow-on formulae, article 1.2 (a), the term "infants" means children under the age of 12 months.

"Pre-term infant" generally means an infant born before 37 weeks gestation.

"Term Born Infant" generally means an infant born after 37 weeks gestation.

"Toddler" generally means a child from when he can walk up to three years old.

"Young mammal" means in the context of the present invention a mammal who has not entered puberty. This corresponds to infancy and childhood in humans and the equivalent age in animals.

"Probiotic" means microbial cell preparations or components or metabolites of microbial cells with a beneficial effect on the health or well-being of the host [Salminen, S. et al. (1999); Probiotics: how should they be defined, Trends Food Sci. Technol., 10 107-10]. The definition of probiotic is generally admitted and in line with the WHO definition. The probiotic can comprise a unique strain of micro-organism, a mix of various strains and/or a mix of various bacterial species and genera. In case of mixtures, the singular term "probiotic" can still be used to designate the probiotic mixture or preparation. For the purpose of the present invention, micro-organisms of the genus *Lactobacillus* are considered as probiotics.

"Prebiotic" generally means a non-digestible food ingredient that beneficially affects the host by selectively stimulating the growth and/or activity of micro-organisms present in the gut of the host, and thus attempts to improve host health.

"Allergy" means an allergy which has been detected by a medical doctor and which can be treated occasionally or in a more durable manner. A "food allergy" is an allergy with respect to a food constituent.

"Infant formulae": according to the Commission Directives 2006/141/EC of 22 Dec. 2006 and/or 91/321/EEC of 14 May 1991 on infant formulae and follow-on formulae, article 1.2 (c), the term "infant formulae" means foodstuffs intended for particular nutritional use by infants during the first four to six months of life and satisfying by themselves the nutritional requirements of this category of persons. It has to be understood that infants can be fed solely with infant formulas, or that the infant formula can be used by the career as a complement of human milk. It is synonymous to the widely used expression "starter formula".

"Follow-on formulae": according to the Commission Directives 2006/141/EC of 22 Dec. 2006 and/or 91/321/EEC of 14 May 1991 on infant formulae and follow-on formulae, article 1.2 (d), the term "follow-on formulae" means foodstuffs intended for particular nutritional use by infants aged over four months and constituting the principal liquid element in a progressively diversified diet of this category of persons.

"Growing-up milk": milk-based nutritional composition especially adapted to a child of between one year and three years old.

"Human Milk fortifier": Nutritional composition for infants or young children intended to be added to or diluted with human milk.

The term "hypoallergenic composition" means a composition which is unlikely to cause allergic reactions.

The term "sialylated oligosaccharide" means an oligosaccharide having a sialic acid residue.

The term "fucosylated oligosaccharide" means an oligosaccharide having a fucose residue.

The expression "nutritional composition" means a composition which nourishes a subject. This nutritional composition is usually to be taken orally or intravenously, and it usually includes a lipid or fat source, a carbohydrate source and a protein source.

In the context of the present invention, the nutritional compositions are typically "synthetic nutritional compositions", i.e. not of human origin (e.g. this is not breast milk). The expression "synthetic nutritional composition" means a mixture obtained by chemical and/or biological means, which can be chemically identical to the mixture naturally occurring in mammalian milks.

In some embodiments of the invention, the nutritional composition is a hypoallergenic nutritional composition. The expression "hypoallergenic nutritional composition" means a nutritional composition which is unlikely to cause allergic reactions.

The nutritional compositions according to the invention may be for example an infant formula, any other milk-based nutritional composition, a supplement (or a complement), a fortifier such as a milk fortifier. The nutritional compositions can be in powder or liquid form.

The term "oligosaccharide" means a carbohydrate having a degree of polymerization (DP) ranging from 2 to 20 inclusive but not including lactose. In some embodiments of the invention, carbohydrate has DP ranging from 3 to 20.

The expressions "oligosaccharide", "oligosaccharides", "oligosaccharide mixture" or "mixture of oligosaccharide(s)" can be used interchangeably. In some advantageous embodiments the oligosaccharides of the oligosaccharide mixture are bovine milk oligosaccharides, bovine milk-derived oligosaccharides, or oligosaccharides derived from bovine milk (all also referred to as "BMOs").

The expression "N-acetylated oligosaccharide" means an oligosaccharide having N-acetyl residue.

The expressions "galacto-oligosaccharide" and "GOS" can be used interchangeably. They refer to an oligosaccharide comprising two or more galactose molecules which has no charge and no N-acetyl residue (i.e. they are neutral oligosaccharide).

The expression "sialylated oligosaccharide" means an oligosaccharide having a sialic acid residue with associated charge.

The term "prebiotic" means a non-digestible food ingredient that beneficially affects the host by selectively stimulating the growth and/or activity of one or a limited number of bacteria in the colon and thus improves host health (Gibson and Roberfroid "Dietary Modulation of the Human Colonic Microbiota: Introducing the Concept of Prebiotics", J. Nutr. 1995: 125(6):1401-1412). "Prebiotics" alternatively means selectively fermented ingredients that allow specific changes, both in the composition and/or activity in the gastrointestinal microflora, that confer benefits upon the host well-being and health (Roberfroid M. "Prebiotics: the concept revisited", J. Nutr. 2007: 37 (3): 830S-837S).

The term "cfu" should be understood as colony-forming unit.

All percentages are by weight unless otherwise stated. The expressions "weight %" and "wt %" are synonymous. They refer to quantities expressed in percent on a dry weight basis.

It is noted that the various aspects, features, examples and embodiments described in the present application may be compatible and/or combined together.

As used in this specification, the words "comprises", "comprising", and similar words, are not to be interpreted in an exclusive or exhaustive sense. In other words, they are intended to mean "including, but not limited to".

Definition of *Streptococcus*: The "*Streptococcus* ssp" as used herein refers to a genus of bacteria within the phylum Firmicutes. The phylum "Firmicutes" comprises bacteria of the classes Bacilli, Clostridia and Mollicutes, and the taxonomic family "Streptococcaceae" eventually comprises, inter alia, the genus of *Streptococcus* ssp.

Measure of Relative Abundance of *Streptococcus*

The abundance of *Streptococcus* in the gut microbiota is provided as a relative measure. It is calculated on the basis of results from a measurement of the composition of bacteria community in the gut which, according to the present invention, is carried out by annotating bacterial 16S rDNA sequences to the Silva database followed by RDP-II Classifier. The skilled person would, however, be able to consider further methods, as appropriate. The proportion of *Streptococcus* in the gut microbiota composition is given as the relative abundance [%].

Description of the Invention

The present invention elaborates on the concept of controlling, manipulating, modifying or otherwise influencing the gut microbiota composition of a subject. One important aspect of this idea is the impact the gut microbiota composition may have on a subject's body weight and health condition, especially later in life.

The inventors have observed a strong correlation between the adiposity gain between birth and 18 months in young subjects and an increased amount of *Streptococcus* bacteria in the gut the subjects.

The inventors propose to solve the problems of the invention by suggesting nutritional interventions with a composition comprising oligosaccharides able to down modulate the specific *Streptococcus* bacteria and hence reduce the risk of obesity later in life. The prebiotic oligosaccharides of the invention have been selected to show the intended effect.

FIG. 1 illustrates the correlation between relative abundance of *Streptococcus* bacteria in the gut of young subjects and the adiposity gain between birth and 18 months: Fecal samples were collected from predominantly mix-fed, healthy infants at the age of 6 months. Fecal microbiota composition was measured by pyrosequencing of variable regions (V4-V5-V6) of the 16S RNA genes present in the microbial population. The subscapular skinfold thickness was measured at birth and at 18 months of age. Subscapular skinfold thickness is considered a precise measure of adiposity. The proportion of *Streptococcus* genus in fecal microbiota was associated with the increase in subscapular skinfold between birth and age of 18 months. The statistical analysis shows a statistically significant correlation.

The inventors have investigated a number of potential nutritional effectors and selected those having the greatest effect on the *Streptococcus* flora in the gut.

FIG. 2 shows that (a) some oligosaccharides are effective to reduce the abundance of *Streptococcus* in the gut and (b) not all nutrients are similarly effective to effect such reduction.

In all experiments, fecal samples were collected and fecal microbiota composition was measured by pyrosequencing of variable regions (V123) of the 16S RNA genes present in the microbial population.

In all experiments subjects were fed with the tested composition for at least 7 days, fecal samples were collected and the relative abundance of *Streptococcus* was measured by pyrosequencing of the 16S RNA genes contained in the extracted samples.

FIG. 2A

Healthy infants received either standard infant formula (NAN-1 infant formula, available commercially in Germany in 2013) or NAN-1 with a mixture of Bovine Milk derived Oligosaccharides (BMOS), and *B. lactis* probiotic. at $1.10^7$ cfu/g. The mixture of BMOS comprises (in the final infant formula, on a dry weight basis) approximately:

N-acetylated oligosaccharides: from 0.006 to 0.24 wt %
Galacto-oligosaccharides: from 5.52 to 5.91 wt %
Sialylated oligosaccharides: from 0.018 to 0.24 wt %

The GOS was commercial "Vivinal GOS" sourced from Friesland Campina (NL). The probiotic *B. lactis* (*Bifidobacterium lactis*) is commercial "BB12" available from CHr. Hansen, Denmark.

The infants were full term and less than 14 days at the time of enrollment. They received the formula, supplemented or not, for 3 months.

Figure 2A:
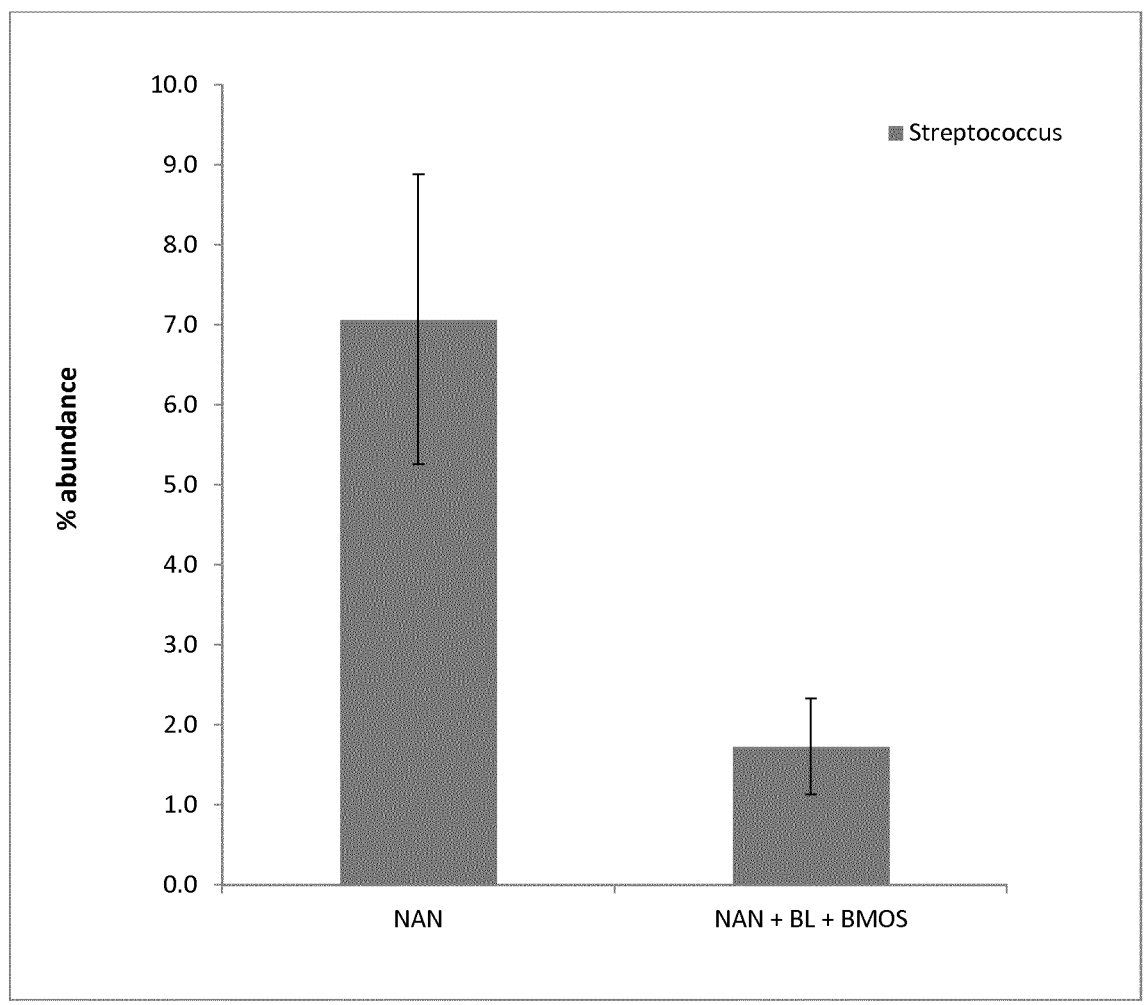
FIG. 2 A, B, C, D illustrate the reduction of *Streptococcus* abundance in populations of subjects receiving various oligosaccharides and related controls.

FIG. 2A shows that the tested oligosaccharide composition has a down regulating effect on the relative abundance of *Streptococcus* in the gut of the subjects.

FIG. 2B.

In this experiment, young (6 weeks) male C57BL/6J mice were used.

After a period of acclimatization of three weeks on low fat diet, the animals were switched to one of the following treatments.

The low fat and high fat diets were obtained from standard low and high fat diets from Research Diets, USA, and were isocaloric (4057 Kcal/Kg).

Control diet: Rodent Diet With 60 kcal % Fat (conventional)

GOS prebiotics diet: Rodent Diet With 60 kcal % Fat and 211 g Fiber Mix (=GOS, The GOS was commercial "Vivinal GOS" sourced from Friesland Campina (NL)). Add to diet 211 g of syrup or 158.2 g of dried powder, for a total of 531 Kcal. In dry matters, 90 g are fibers (258 Kcal), and 68.2 g are sugars (272.8 Kcal). To maintain isocaloric balance between the different diets in the different groups, 258 Kcal were removed from maltodextrin, and 272.8 Kcal from sucrose.

BMOS prebiotics diet: Rodent Diet With 60 kcal % Fat and 140 g Fiber Mix (=BMOS, same as referred to in FIG. 2A). Add to diet 140 g of powder, for a total of 350 Kcal. In dry matters, 35.7 g are fibers (71.4 Kcal), and remaining 278.6 Kcal are from Sugars. To maintain isocaloric balance between the different diets in the different groups, 75 Kcal were removed from maltodextrin, and 275 Kcal from sucrose.

Inulin and fructooligosaccharides (FOS) diet: Rodent Diet With 60 kcal % Fat and 100 g Fiber Mix. For 100 g product, add 30 g of product FOS to 70 g of Inulin (FOS was P95 Raftilose. Inulin was conventional Inulin commercially available. FOS and Inulin are commercially available from for example Beneo-Orafti, Belgium/Netherland) Add to diet 100 g of mix. In dry matters, 90 g are fibers (116 Kcal), and 10 g are sugars (40 Kcal). To maintain isocaloric balance between the different diets in the different groups, 116 Kcal were removed from maltodextrin, and 40 Kcal from sucrose.

Sugars diet: Rodent Diet With 60 kcal % Fat and 35.1 g Dextrose, 32.3 g Lactose and 1.45 g galactose. Mix is composed at 51% by glucose, 47% by lactose and 2% by galactose. Add to diet, 68.75 g of Mix, i.e. 275 Kcal. (35.1 g glucose, 32.3 g lactose, 1.45 g galactose). To maintain isocaloric balance between the different diets in the different groups, 275 Kcal were removed from sucrose.

Figure 2B:
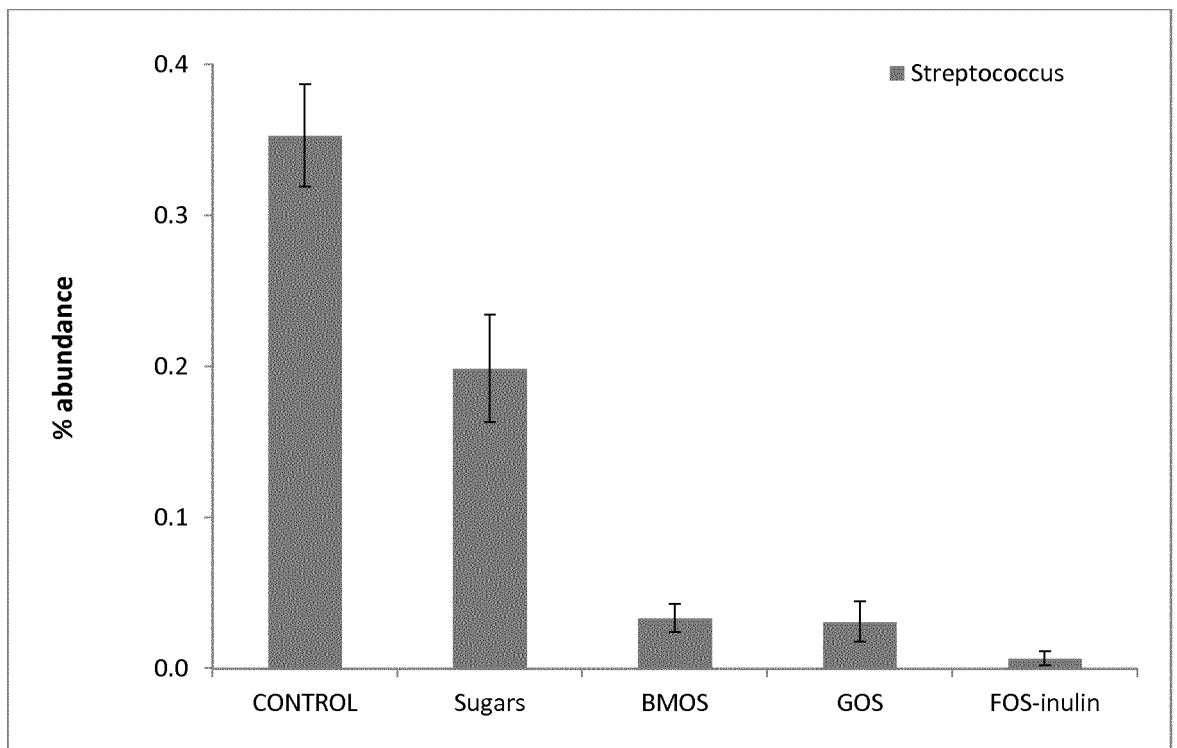

FIG. 2B shows that the tested oligosaccharide composition has a down regulating effect on the relative abundance of *Streptococcus* in the gut of the subjects.

FIG. 2C:

Obese adult volunteers under moderate calorie restriction received the probiotic LPR and FOS-inulin. The change in fecal microbiota was assessed after 29 days of treatment. The probiotic capsules contained a formulation consisting of 10 mg of a LPR powder providing $1.62 \times 10^8$ cfu, 300 mg of a mix of oligofructose and inulin (70:30, v/v) and 3 mg of magnesium stearate. The subjects consumed two capsules per day. LPR is *Lactobacillus rhamnosus* CGMCC1.3724.

Figure 2C:
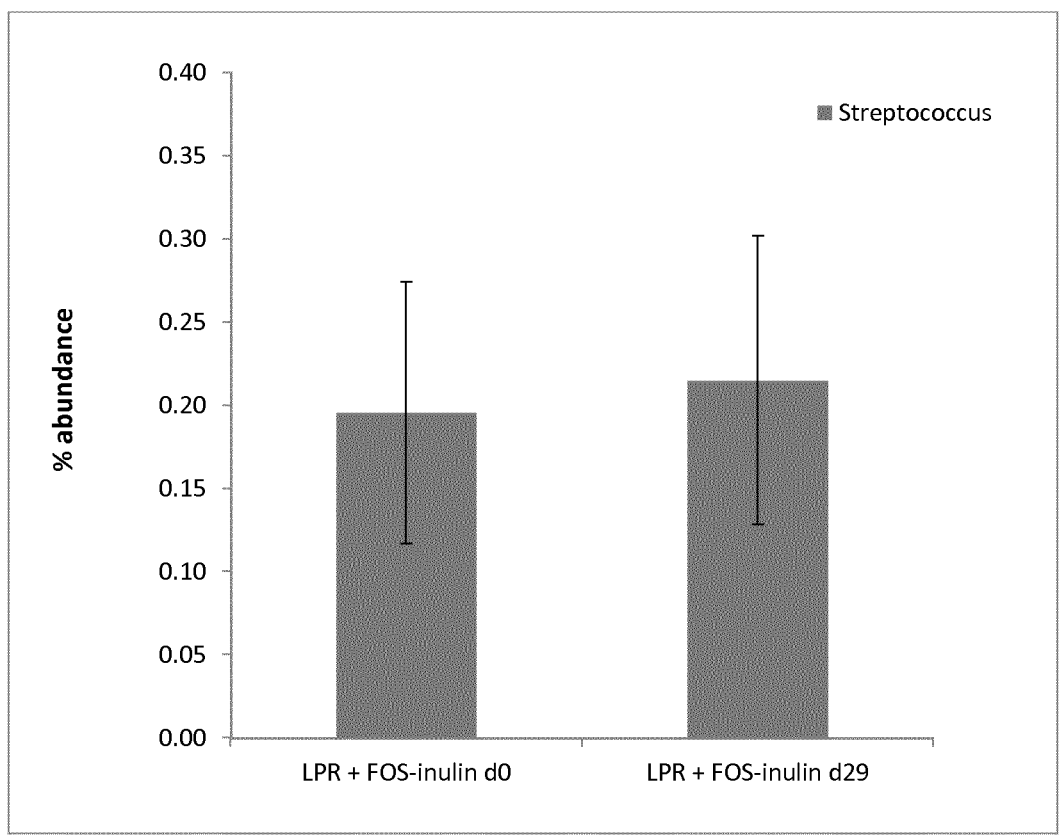

FIG. 2C show that the tested probiotic and low dose of prebiotic had no effect on the abundance of *Streptococcus* in adult.

FIG. 2D.

Healthy infants received either an infant formula (65 kcal/100 g, 2.25 g/100 kcal protein, 5.6 g/100 kcal fat, low dose probiotics $5 \times 10^4$ cfu/g *Bifidobacterium lactis* strain CNCM I-3446, 1 g/l native lactoferrin) or the same formula with a mixture of Bovine Milk Oligosaccharides (BMOS) at 5 g/l. (same BMOS as for FIG. 2A) The infants were full term and less than 14 days at the time of enrollment. They received the formula, supplemented with BMOS or not, for 1 week.

Figure 2D:
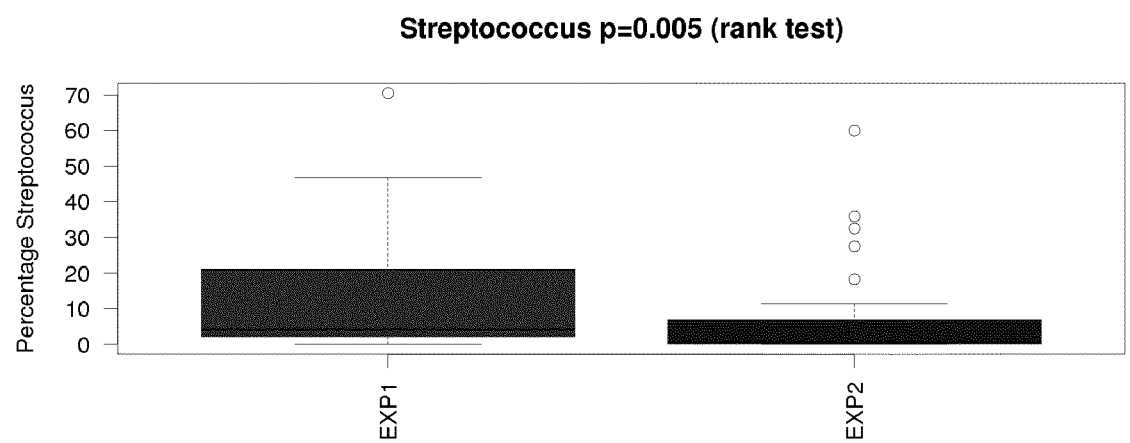

FIG. 2D shows that, compared to the control infant formula (EXP1) the formula supplemented with BMOS (EXP2) has a down regulating effect on the relative abundance of *Streptococcus* in the gut of the infants.

It has been repeatedly observed that healthy predominantly breast-fed infants of diverse ethnicities had low level (of less than 2.5%) of *Streptococcus* at the age of 5 to 6 months (Yatsunenko, et al., Nature 2012 Jun. 14; 486: 222-228, Figure S20; Koren, et al., Cell 2012 Aug. 3; 150: 470-480).

Without to be bound by the theory, it is believed that oligosaccharides suppress *Streptococcus*, because they provide suboptimal substrate for its growth. This allows other, more beneficial bacteria to reach higher abundance, which in turn modify the environmental conditions to create unfavorable growth conditions for *Streptococcus*.

Embodiments of the Invention

In one embodiment of the invention the composition comprises a prebiotic oligosaccharide that is effective to down regulate the occurrence/count of *Streptococcus* in the gut of infants. Such oligosaccharide can for example be polyfructose, long chain fructo-oligosaccharides, short-chain fructo-oligosaccharides (for example with degree of polymerisation (DP) between 2 and 8), inulin, galacto-oligosaccharides, sialylated-oligosaccharides, fucosylated oligosaccharides, and mixture of thereof.

In one preferred embodiment the oligosaccharides are mixtures of sialylated oligosaccharides and GOS.

In one embodiment the oligosaccharide of the invention are present in the composition in an amount of between 0.5 and 10 g/100 kcal, preferably between 1 and 5 g/100 kcal, most preferably between 2 and 4 g/100 kcal.

In one embodiment the oligosaccharides are present in the composition in an amount of at least 0.5 w %, 1 wt %, at least 5 wt % or at least 10 wt %.

In one embodiment the oligosaccharides are present in the composition in an amount of between 0.5 w % and 10 wt %, or between 1 wt % and 5 wt %.

In one embodiment the mixture of oligosaccharides comprises N-acetylated oligosaccharides, Galacto-oligosaccharides (GOS), and Sialylated oligosaccharides.

In one embodiment the composition comprises:
N-acetylated oligosaccharides between 0.001 to 1 wt %, preferably between 0.003 wt % and 0.3 wt %
Galacto-oligosaccharides between 1 and 10 wt %, preferably between 3 and 6 wt %
Sialylated oligosaccharides between 0.005 and 1 wt %, preferably between 0.01 and 0.4 wt %

In one most preferred embodiment the oligosaccharide of the composition of the invention consist of or comprises at least one N-acetylated oligosaccharide, at least one galacto-oligosaccharide and at least one sialylated oligosaccharide.

The N-acetylated oligosaccharide is an oligosaccharide having an N-acetylated residue. Suitable N-acetylated oligosaccharides of the oligosaccharide mixture of the nutritional composition according to the present invention include GalNAcβ1,3Galβ1,4Glc and Galβ1,6GalNAcβ1,3Galβ1,4Glc, but also any mixture thereof. The N-acetylated oligosaccharides may be prepared by the action of glucosaminidase and/or galactoaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced by fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerization (DP) from DP=1 onwards. Another option is the chemical conversion of keto-hexose (fructose) either free or bound to an oligosaccharide (e.g lactulose) into N-acetyl-hexosamine or an N-acetylhexosamine containing oligosaccharide as described in Wrodnigg, T. M, Dtutz, A. E, Angew. Chem. Int. Ed. 1999: 38: 827-828.

The galacto-oligosaccharide is an oligosaccharide comprising two or more galactose molecules which has no charge and no N-acetyl residue. Suitable galacto-oligosaccharides of the oligosaccharide mixture of the nutritional composition according to the present invention include Galβ1,3Galβ1,4Glc, Galβ1,6Galβ1,4Glc, Galβ1,3Galβ1,3Galβ1,4Glc, Galβ1,6Galβ1,6Galβ1,4Glc, Galβ1,3Galβ1,6Galβ1,4Glc, Galβ1,6Galβ1,3Galβ1,4Glc, Galβ1,6Galβ1,6Galβ1,6Glc, Galβ1,3Galβ1,3Glc, Galβ1,4Galβ1,4Glc and Galβ1,4Galβ1,4Galβ1,4Glc, but also any mixture thereof. Synthesized galacto-oligosaccharides such as Galβ1,6Galβ1,4Glc, Galβ1,6Galβ1,6Galβ1,6Glc, Galβ1,3Galβ1,4Glc, Galβ1,6Galβ1,6Galβ1,4Glc, Galβ1,6Galβ1,3Galβ1,4Glc, Galβ1,3Galβ1,6Galβ1,4Glc, Galβ1,4Galβ1,4Glc and Galβ1,4Galβ1,4Galβ1,4Glc and mixture thereof are commercially available under trademarks Vivinal® and Elix'or®. Other suppliers of oligosaccharides are Dextra Laboratories, Sigma-Aldrich Chemie GmbH and Kyowa Hakko Kogyo Co., Ltd. Alternatively, specific glycotransferases, such as galoctosyltransferases may be used to produce neutral oligosaccharides.

The sialylated oligosaccharide is an oligosaccharide having a sialic acid residue with associated charge. Suitable sialylated oligosaccharides of the oligosaccharide mixture of the nutritional composition according to the present invention include NeuAcβ2,3Galβ1,4Glc and NeuAcβ2,6Galβ1,4Glc, but also any mixture thereof. These sialylated oligosaccharides may be isolated by chromatographic or filtration technology from a natural source such as animal milks. Alternatively, they may also be produced by biotechnology using specific sialyltransferases either by enzyme based fermentation technology (recombinant or natural enzymes) or by microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerization (DP) from DP=1 onwards.

In one aspect of the invention, the nutritional composition comprises the oligosaccharide mixture in an amount from 1% or 2.5% to 15 wt %. Alternatively, the nutritional composition comprises the oligosaccharide mixture in an amount from 3 to 15 wt %, or in an amount from 3 to 10 wt %, or in an amount from 3.5 to 9.5 wt % or in an amount from 4 to 9 wt % or in an amount from 4.5 to 8.5 wt %, or in an amount from 5.0 to 7.5 wt % or in an amount from 5 to 8 wt %.

In some specific embodiments, the nutritional composition may comprise the oligosaccharide mixture in an amount from 0.5 to 3.1 g/100 kcal, or in an amount from 0.6 to 3.1 g/100 kcal, or in an amount from 0.6 to 2.0 g/100 kcal, or in an amount from 0.7 to 2.0 g/100 kcal, or in an amount from 0.8 to 1.8 g/100 kcal, or in an amount from 0.9 to 1.7 g/100 kcal, or in an amount from 1.0 to 1.5 g/100 kcal or in an amount from 1.0 to 1.6 g/100 kcal.

The nutritional composition of the present invention may comprise at least 0.01 wt % of N-acetylated oligosaccharide(s), at least 2.0 wt % of galacto-oligosaccharide(s) and at least 0.02 wt % of sialylated oligosaccharide(s).

In some embodiments, the nutritional composition according to the present invention may comprise at least 0.01 wt %, or at least 0.02 wt %, or at least 0.03 wt %, or at least 0.04 wt %, or at least 0.05 wt %, or at least 0.06 wt % or at least 0.07 wt % of N-acetylated oligosaccharide(s). In some embodiments, it may comprise from 0.01 to 0.07 wt % of N-acetylated oligosaccharide(s) such as from 0.01 to 0.05 wt % of N-acetylated oligosaccharide(s) or from 0.01 to 0.03 wt % of N-acetylated oligosaccharide(s).

In addition, the nutritional composition may comprise at least 2 wt %, or at least 3 wt %, or at least 4 wt %, or at least 5 wt %, or at least 5.5 wt %, or at least 6 wt % or at least 7 wt % or at least 8 wt % of galacto-oligosaccharide(s). In some embodiments, it may comprise from 5 to 8 wt % of galacto-oligosaccharide(s) such as from 5.75 to 7 wt % of galacto-oligosaccharide(s) or from 5.85 to 6.5 wt % of galacto-oligosaccharide(s). A particular example is an amount of 5.95 wt % of oligosaccharide(s).

Finally, the nutritional composition may comprise at least 0.02 wt %, or at least 0.03 wt %, or at least 0.04 wt %, or at least 0.05 wt %, or at least 0.06 wt %, or at least 0.07 wt %, or at least 0.08 wt % or at least 0.09 wt % of sialylated oligosaccharides. In some embodiments, it may comprise from 0.02 to 0.09 wt % of sialylated oligosaccharide(s) such as from 0.02 to 0.08 wt % of sialylated oligosaccharide(s), or from 0.02 to 0.07 wt % of sialylated oligosaccharide(s) or from 0.003 to 0.07 wt % of sialylated oligosaccharide(s).

In a particular embodiment, the nutritional composition according to the present invention may comprise from 0.01 to 0.07 wt % of N-acetylated oligosaccharide(s), from 2.0 to 8.0 wt % of galacto-oligosaccharide(s) and from 0.02 to 0.09 wt % of sialylated oligosaccharide(s).

In yet another particular embodiment, the nutritional composition according to the present invention may comprise from 0.01 to 0.03 wt % of N-acetylated oligosaccharide(s), 5.95 wt % galacto-oligosaccharide(s) and from 0.02 to 0.09 wt % of sialylated oligosaccharide(s).

In another embodiment, the nutritional composition may comprise at least 0.0015 g/100 kcal of N-acetylated oligosaccharide(s), at least 0.70 g/100 kcal of galacto-oligosaccharide(s) and at least 0.0045 g/100 kcal of sialylated oligosaccharide(s).

In some specific embodiments, the nutritional composition may comprise at least 0.0015 g/100 kcal, or at least 0.002 g/100 kcal, or at least 0.0025 g/100 kcal, or at least 0.003 g/100 kcal, or at least 0.0035 g/100 kcal, or at least 0.004 g/100 kcal, or at least 0.0045 g/100 kcal or at least 0.005 g/100 kcal of N-acetylated oligosaccharide(s). In some embodiments, the nutritional composition may comprise from 0.0015 to 0.005 g/100 kcal of N-acetylated oligosaccharide(s) such as from 0.0015 to 0.045 g/100 kcal of N-acetylated oligosaccharide(s) or from 0.002 to 0.0045 g/100 kcal of N-acetylated oligosaccharide(s).

In addition the nutritional composition may comprise at least 0.70 g/100 kcal, or at least 0.74 g/100 kcal, or at least 0.8 g/100 kcal, or at least 0.85 g/100 kcal, or at least 0.90 g/100 kcal, or at least 0.95 g/100 kcal, or at least 1.0 g/100 kcal, or at least 1.05 g/100 kcal, or at least 1.10 g/100 kcal, or at least 1.20 g/100 kcal or at least 1.50 of galacto-oligosaccharide(s). In some embodiments, it may comprise from 0.70 to 1.5 g/100 kcal of galacto-oligosaccharide(s) such as from 0.70 to 1.20 g/100 kcal of galacto-oligosaccharide(s) or from 0.74 to 1.2 g/100 kcal of galacto-oligosaccharide(s). Finally the nutritional composition may comprise at least 0.0045 g/100 kcal, or at least 0.005 g/100 kcal, or at least 0.0055 g/100 kcal, or at least 0.006 g/100 kcal, or at least 0.0065 g/100 kcal, or at least 0.007 g/100 kcal, or at least 0.0075 g/100 kcal, or at least 0.008 g/100 kcal or at least 0.0085 g/100 kcal of sialylated oligosaccharide(s). In some embodiments, it may comprise from 0.0045 to 0.0085 g/100 kcal of sialylated oligosaccharide(s) such as from 0.0045 to 0.008 g/100 kcal of sialylated oligosaccharide(s) or from 0.0045 to 0.0075 g/100 kcal of sialylated oligosaccharide(s).

In a particular embodiment, the nutritional composition may comprise from 0.0015 to 0.005 g/100 kcal of N-acetylated oligosaccharide(s), from 0.70 to 1.5 g/100 kcal of galacto-oligosaccharide(s) and from 0.0045 to 0.0085 g/100 kcal of sialylated oligosaccharide(s).

In another particular embodiment, the nutritional composition may comprise from 0.0015 to 0.0045 g/100 kcal of N-acetyl-oligosaccharide(s), from 0.74 to 1.2 g/100 kcal of galacto-oligosaccharide(s) and from 0.0045 to 0.0075 g/100 kcal of sialylated oligosaccharide(s).

In a particular advantageous embodiment, the oligosaccharide mixture of the nutritional composition according to the invention comprises from 0.1 to 4.0 wt % of N-acetylated oligosaccharide(s), from 92.0 to 98.5 wt % of the galacto-oligosaccharide(s) and from 0.3 to 4.0 wt % of the sialylated oligosaccharide(s).

Source of Prebiotics:

The oligosaccharides can be isolated from any source. Preferably the oligosaccharides are isolated, purified or concentrated from bovine milk. Alternatively all or some of the oligosaccharides are produced in totality or in part by bioengineering.

Conventional technologies for fractioning and enriching bovine milk fractions in Bovine Milk derived Oligosaccharides can be used (such conventional technologies include column filtration, resin-filtration, nano-filtration, enzymatic treatment specially with beta-galactosidase, precipitation of proteins, crystallisation and separation of lactose etc, . . . ). Some fractions of bovine milk enriched in oligosaccharides are commercially available or have been described (for example in EP2526784 A1 which process can be used to provide the oligosaccharide mixture used by the present invention).

Reduction of *Streptococcus*

In various embodiments of the invention the reduction (or down regulation) of *Streptococcus* in accordance with the invention refers to either:

the reduction of the absolute count of *Streptococcus* in the gut of the infant, and/or the relative reduction of the proportion of *Streptococcus* over the whole microbiota in the gut of the infant. This proportion of *Streptococcus* in the gut microbiota composition of a subject may be reduced by at least 10%, at least 25%, at least 50%, or at least 80%. compared to the initial proportion of *Streptococcus* in the gut microbiota of the subject before the administration of the composition, or in comparison to the average The "reduction or down regulation" refers to a statistically significant ($p<0.05$) reduction in respect to the average count or proportion of *Streptococcus* bacteria in healthy, vaginally-born, breast fed infants of the same age, preferably a reduction of at least 10%, at least 30% or at least 50%.

Alternatively in one embodiment the "reduction or down regulation" refers to a statistically significant ($p<0.05$) reduction in respect to the initial count or proportion of *Streptococcus* in the gut microbiota of the subject before the administration of the composition, preferably a reduction of at least 10%, at least 30% or at least 50%.

Target Group

In one embodiment of the invention the infants are healthy infants. In one preferred embodiment the infants are infants in needs, i.e infant having a higher than average risk of developing excessive adiposity, overweight or obesity later in life.

In one embodiment the infants in needs (who can benefit from the invention) are infants exhibiting a higher count of *Streptococcus* bacteria in the gut (and/or a general unbalanced gut flora). A "higher count" of *Streptococcus* bacteria refers to a count (or a proportion) that is statistically higher than the average count (or proportion or "abundance" or "relative abundance") of *Streptococcus* bacteria in healthy, vaginally-born, breast fed infants of the same age. Preferably the "high count" refers to a count that is at least 10%, at least 30% or at least 50% higher.

In one embodiment the infants are infants receiving a synthetic nutritional composition such as infant formula or follow-on formula in an amount corresponding to at least 50% or at least 70% of their daily caloric intake. Such infant can be prone to have an unbalanced gut flora, in particular with a higher count of *Streptococcus* bacteria in the gut (compared to average count of *Streptococcus* bacteria in healthy, vaginally-born, breast fed infants of the same age).

In one embodiment of the invention the composition is use among a target group of infants born by Caesarean-section (C-section). Infant born by C-section are known to have a different gut flora compared to infant born by vaginal delivery. The microbiota of C-section infants evolves therefore differently over age compared to vaginally-born infants. In some cases the inventors have found that C-section infants may exhibit a count of *streptococcus* that is higher than vaginally-born infants. Such infants may then benefit of the invention.

In one embodiment the invention applies to non-human young mammals, young pets, young cat or young dogs (in that case the embodiments describes for "infants" apply to the subjects young mammals).

Timing and Duration of Administration:

In one embodiment the composition of the invention is provided to the subject infants during or at least during the first 4 weeks, first 8 weeks, first 3 months or first 6 months of life. Preferably the composition is provided as the primary or sole source of nutrition to the infants during said period. Alternatively the composition is provided such as to correspond to at least 50%, at least 70% or at least 90% of the total caloric intake of said infant during said period.

The composition of the present invention is particular beneficial for long term application. Consequently, a preparation comprising the agent may be administered for at least 2 weeks, at least 3 weeks, at least 4 weeks, at least 5 weeks, at least 6 weeks, at least 7 weeks, and/or at least 8 weeks.

Duration of Effect of the Administration of the Composition:

The reduction of *streptococcus* can be observed short after the beginning of the administration (e.g. 4 to 20 days after the beginning of the administration) and can remain during 2 to 10 days at the end of the administration. Usually however the reduction of *Streptococcus* can better observed after a longer period of administration (e.g. 2 to 4 months or more). Preferably the reduction of *streptococcus* remains for an extended period of time because a new microbiota equilibrium has been established. For example the reduction can still be observed 1, 2, 6 months or more after the end of the administration. Such long term effect is at the base of the long term effect on obesity and adiposity. It is believed that the establishment of a new balance in the microbiota has a programming effect on the future microbiota and on the overall metabolic pathways (such as the fatty acid metabolism).

Prevention of Obesity/Adiposity Later in Life/Overweight

The invention indirectly promotes the reduction of the count of *Streptococcus* bacteria is such as to promote the reduction/prevention of obesity and/or adiposity later in life and/or overweight later in life.

Such obesity can be characterized by a Body Mass Index (BMI) of 30 or more. In one embodiment the considered BMI is at the age of 18, 15, 10, 5 or 3 years of life.

In one embodiment the reduction of the count of *Streptococcus* bacteria is such as to promote the reduction/prevention of overweight. Such overweight is characterized by a BMI of between 25 and 29.9 (considered at the same age as above).

In one embodiment the reduction of the count of *Streptococcus* bacteria is such as to promote the reduction/prevention of adiposity. Such adiposity is defined by an exaggerated tendency to accumulate fat mass. For example such adiposity can be characterized by the accumulation of fat mass that is 30% or 50% above the average of a standard non-obese healthy population of the same age. Overweight is defined as conventionally acknowledged in reference to BMI.

The prevention/reduction of adiposity/obesity/overweight later in life can be mediated via influencing the weight gain, during infancy and more particularly the adiposity gain.

Probiotics:

In one embodiment the composition of the invention further comprises probiotics. Preferably such probiotics act in a synergistic way with the oligosaccharide prebiotics to reduce the count of *streptococcus*. Such promotion of the reduction of *Streptococcus* can be direct by competing with or inhibiting the growth of *Streptococcus*, or can be indirect by establishing a balanced microbiota in which *Streptococcus* have a lower proportion. (e.g. by favouring other bacteria). Probiotic bacteria may be selected from the group consisting of *Bifidobacterium, Lactobacillus, Lactococcus, Enterococcus, Deuteromycota, Debaryomyces, Kluyveromyces, Saccharomyces, Yarrowia, Zygosaccharomyces, Candida*, and *Rhodotorula*; preferentially lactic acid bacteria and bifidobacteria, or mixtures thereof; and/or in particular may be selected from the group consisting of *Bifidobacterium longum, Bifidobacterium lactis, Bifidobacterium animalis, Bifidobacterium breve, Bifidobacterium infantis, Lactobacillus acidophilus, Lactobacillus casei, Lactobacillus salivarius, Lactococcus lactis, Lactobacillus reuteri, Lactobacillus rhamnosus, Lactobacillus paracasei, Lactobacillus johnsonii, Lactobacillus plantarum, Lactobacillus salivarius, Enterococcus faecium, Saccharomyces cerevisia, Saccharomyces boulardii* or mixtures thereof, preferably selected from the group consisting of *Lactobacillus johnsonii* (NCC533; CNCM I-1225), *Bifidobacterium longum* (NCC490; CNCM I-2170), *Bifidobacterium longum* (NCC2705; CNCM I-2618), *Bifidobacterium lactis* (NCC2818; CNCM I-3446), *Lactobacillus paracasei* (NCC2461; CNCM I-2116), *Lactobacillus rhamnosus* (GG; ATCC53103), *Lactobacillus rhamnosus* (NCC4007; CGMCC 1.3724; LPR), *Enterococcus faecium* (SF 68; NCIMB10415), and mixtures thereof.

*Lactobacillus johnsonii* NCC533 was deposited on 30 Jun. 1992 with the CNCM, has received accession number CNCM I-1225. *Bifidobacterium longum* NCC490 was deposited on 15 Mar. 1999 with the CNCM, has received accession number CNCM I-2170. *Bifidobacterium longum* NCC2705 was deposited on 29 Jan. 2001 with the CNCM, has received accession number CNCM I-2618. *Bifidobacterium lactis* NCC2818 was deposited on 7 Jun. 2005 with the CNCM, has received accession number CNCM I-3446. *Lactobacillus paracasei* NCC2461 was deposited on 12 Jan. 1999 with the CNCM, has received accession number CNCM I-2116. CNCM refers to the Collection nationale de cultures de micro-organismes (CNCM), Institut Pasteur, 28, rue du Dr Roux, F-75724 Paris Cedex 15, France. *Lactobacillus rhamnosus* NCC4007, was deposited in Oct. 2004, with the China General Microbiological Culture Collection Center (CGMCC), Institute of Microbiology, Chinese Academy of Sciences, No. 1, West Beichen Road, Chaoyang District, Beijing 100101, China, and has received accession number CGMCC 1.3724. Both CNCM and CGMCC are depositary institutions having acquired the status of international depositary authority under the Budapest Treaty on the International Recognition of the Deposit of Microorganisms for the Purposes of Patent Procedure.

The dosage of probiotics can be for example between $10^5$ and $10^{12}$ cfu per gram of composition, preferably in an amount sufficient to deliver a synergistic effect with the oligosaccharides of the composition, and preferably between $10^6$ and $10^8$ cfu/g of composition.

Composition Matrix/Infant Formula Matrix:

The composition of the invention may contain any known and useful ingredient of the art. The daily doses of composition and of each individual ingredient administered should always comply with the published safety guidelines and regulatory requirements. This is particularly important with respect to the administration to new-born babies, especially those born with low birth weight, very low or extremely low birth weight.

Infant formulas may contain a protein source in an amount of not more than 4.0, 3.0 or 2.0 g/100 kcal, preferably 1.8 to 2.0 g/100 kcal, less than 1.8 g/100 kcal or between 1.5 and 1.8 g/100 kcal. The type of protein is not believed to be critical to the present invention provided that the minimum requirements for essential amino acid content are met and satisfactory growth is ensured although it is preferred that over 50% by weight of the protein source is whey. In one embodiment, the protein content is between 30% and 80% whey proteins. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in whatever proportions are desired. In one embodiment the proteins originate from bovine milk and the cGMP level has been reduced in comparison to the corresponding original bovine milk.

The proteins may be intact or hydrolyzed or a mixture of intact and hydrolyzed proteins. It may be desirable to supply partially hydrolyzed proteins (degree of hydrolysis between 2 and 20%), for example for infants believed to be at risk of developing cows' milk allergy. If hydrolyzed proteins are required, the hydrolysis process may be carried out as desired and as is known in the art. For example, a whey protein hydrolysate may be prepared by enzymatically hydrolyzing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

The composition may also comprise a source of carbohydrates and/or a source of fat. The infant formula may contain a source of lipids. The lipid source may be any lipid or fat which is suitable for use in infant formulas. Preferred fat sources include palm olein, milk fat, high oleic sunflower oil and high oleic safflower oil. The essential fatty acids, linoleic and α-linolenic acid may also be added as small amounts of oils containing high quantities of preformed arachidonic acid and docosahexaenoic acid such as fish oils or microbial oils. In total, the fat content is preferably such as to contribute between 30 to 55% of the total energy of the formula. The fat source preferably has a ratio of n-6 to n-3 fatty acids of about 5:1 to about 15:1, for example about 8:1 to about 10:1.

An additional source of carbohydrate may be added to the nutritional composition. It preferably provides about 40% to about 80% of the energy of the nutritional composition. Any suitable carbohydrate may be used, for example sucrose, lactose, glucose, fructose, corn syrup solids, maltodextrin, or a mixture thereof.

Examples of minerals, vitamins and other nutrients optionally present in the infant formula include vitamin A, vitamin B1, vitamin B2, vitamin B6, vitamin B 12, vitamin E, vitamin K, vitamin C, vitamin D, folic acid, inositol, niacin, biotin, pantothenic acid, choline, calcium, phosphorous, iodine, iron, magnesium, copper, zinc, manganese, chloride, potassium, sodium, selenium, chromium, molybdenum, taurine, and L-carnitine. Minerals are usually added in salt form. The presence and amounts of specific minerals and other vitamins will vary depending on the intended infant population.

The infant formula may optionally contain other substances which may have a beneficial effect such as fibers, lactoferrin, nucleotides, nucleosides, and the like. One or more essential long chain fatty acids (LC-PUFAs) may be included in the composition. Examples of LC-PUFAs that may be added are docosahexaenoic acid (DHA) and arachidonic acid (AA). The LC-PUFAs may be added at concentrations so that they constitute greater than 0.01% of the fatty acids present in the composition.

One or more food grade emulsifiers may be included in the nutritional composition if desired; for example diacetyl tartaric acid esters of mono- and di-glycerides, lecithin and mono- or di-glycerides or a mixture thereof. Similarly, suitable salts and/or stabilisers may be included. Flavours can be added to the composition.

The composition of the invention is preferably orally or enterally administrable; for example in the form of a powder for re-constitution with milk or water.

Preferably, the preparation is provided in the form of a powder, e.g., a shelf stable powder. Shelf stability can be obtained, for example by providing the composition with a water activity smaller than 0.2, for example in the range of 0.19-0.05, preferably smaller than 0.15.

Water activity or $a_w$ is a measurement of the energy status of the water in a system. It is defined as the vapor pressure of water divided by that of pure water at the same temperature; therefore, pure distilled water has a water activity of exactly one.

The preparation may be prepared in any suitable manner. For example, it may be prepared by blending together the protein, the carbohydrate source, and the fat source in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently about 50° C. to about 80° C. to aid dispersal of the ingredients. Commercially available liquefiers may be used to form the liquid mixture. The liquid mixture is then homogenised; for example in two stages.

The liquid mixture may then be thermally treated to reduce bacterial loads, by rapidly heating the liquid mixture to a temperature in the range of about 80° C. to about 150° C. for about 5 seconds to about 5 minutes, for example. This may be carried out by steam injection, autoclave or by heat exchanger; for example a plate heat exchanger.

Then, the liquid mixture may be cooled to about 60° C. to about 85° C.; for example by flash cooling. The liquid mixture may then be again homogenised; for example in two stages at about 10 MPa to about 30 MPa in the first stage and about 2 MPa to about 10 MPa in the second stage. The homogenised mixture may then be further cooled to add any heat sensitive components; such as vitamins and minerals. The pH and solids content of the homogenised mixture are conveniently adjusted at this point.

The homogenised mixture is transferred to a suitable drying apparatus such as a spray drier or freeze drier and converted to powder. The powder should have a moisture content of less than about 5% by weight.

Example 1

An example of the composition of an infant formula for use according to the present invention is given below. This composition is given by way of illustration only. The protein source is a mixture of 60% MSWP28 and 40% casein.

| Nutrient | per 100 kcal | per litre |
| --- | --- | --- |
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Prebiotic oligosaccharides | | |
| GOS (g) and/or | 0.64 | 4.3 |
| BMOS (g) (as defined for FIG. 2A) or combination thereof | 1.1 | 7.5 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (µg) | 8 | 50 |
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| Probiotic: Bifidobacterium lactis NCC2818 (CNCM I-3446), | $2 \times 10^7$ cfu/g of powder | |

The invention claimed is:

1. A method for reducing a count of Streptococcus bacteria in the gut in a formula-fed infant having a higher than average risk of developing a condition later in life selected from the group consisting of excessive adiposity, overweight and obesity, the method comprising administering a synthetic nutritional composition comprising prebiotic oligosaccharides to the infant, wherein the prebiotic oligosaccharides comprise N-acetylated oligosaccharides, Sialylated oligosaccharides, and Galacto-oligosaccharides,
wherein the infant to whom the synthetic nutritional composition is administered has a count of Streptococcus bacteria in the gut, before the administering of the synthetic nutritional composition, that is at least 10% higher than the average count of Streptococcus bacteria in healthy vaginally-born breast fed infants of the same age,
wherein the N-acetylated oligosaccharides are 0.0015 to 0.005 g/100 kcal of the synthetic nutritional composition, the Galacto-oligosaccharides are 0.70 to 1.5 g/100 kcal of the synthetic nutritional composition, and the Sialylated oligosaccharides are 0.0045 to 0.0085 g/100 kcal of the synthetic nutritional composition.

2. The method of claim 1 wherein the reduction of the count of Streptococcus bacteria in the gut is a reduction of at least 20% with respect to the average abundance observed in the same population of infants before taking said composition.

3. The method of claim 1 wherein the count of Streptococcus bacteria in the gut of the infant before the administering of the synthetic nutritional composition to the infant is at least 30% higher than the average count of Streptococcus bacteria in a population of healthy vaginally-born breast-fed infants of the same age.

4. The method of claim 1 wherein the infant was born by C-section.

5. The method of claim 1 wherein the synthetic nutritional composition is administered to the infant in an amount effective to reduce a risk of obesity later in life as characterized by an BMI index of 30 or more at the age of 18.

6. The method of claim 1 wherein the synthetic nutritional composition comprises a probiotic further enhancing the reduction of the count of streptococcus bacteria in the gut.

7. The method of claim 6 wherein the probiotic is selected from the group consisting of: Bifidobacterium longum, Bifidobacterium lactis, Bifidobacterium animalis, Bifidobacterium breve, Bifidobacterium infantis, Lactobacillus acidophilus, Lactobacillus casei, Lactococcus lactis, Lactobacillus rhamnosus, Lactobacillus paracasei, Lactobacillus johnsonii, Lactobacillus salivarius, and combinations thereof.

8. The method of claim 1 wherein the synthetic nutritional composition comprises a protein source, a lipid source, and a carbohydrate source, the carbohydrate source comprising lactose or maltodextrin or a combination thereof.

9. The method of claim 8 wherein the protein source is selected from the group consisting of hydrolysed proteins, extensively hydrolysed proteins, sweet whey, modified sweet whey with low cGMP, milk-derived proteins with a whey:casein ratio of 60:40 to 100:0, and combinations thereof.

10. The method of claim 1 wherein the synthetic nutritional composition has a formulation selected from the group consisting of (i) a dry powder comprising at least 1 g of the oligosaccharides/100 kcal of the dry powder and (ii) a ready to drink liquid comprising at least 1 g of the oligosaccharides/100 ml of the ready to drink liquid.

11. The method of claim 1 wherein the synthetic nutritional composition is administered to the infant during a time period comprising the first four weeks of life of the infant and provides at least 50% of the total caloric intake of the infant during the time period.

12. The method of claim 1 wherein the synthetic nutritional composition is administered to the infant during a time period comprising the first six months of life of the infant and provides at least 90% of the total caloric intake of the infant during the time period.

13. The method of claim 1 wherein the count of Streptococcus bacteria in the gut of the infant before the administering of the synthetic nutritional composition to the infant is at least 50% higher than the average count of Streptococcus bacteria in a population of healthy vaginally-born breast-fed infants of the same age.

14. The method of claim 6 wherein the synthetic nutritional composition comprises between $10^5$ and $10^{12}$ cfu of the probiotic per gram of the synthetic nutritional composition.

15. The method of claim 1 wherein the prebiotic oligosaccharides consist of the N-acetylated oligosaccharides, the Galacto-oligosaccharides and the Sialylated oligosaccharides.

16. The method of claim 6 wherein the synthetic nutritional composition comprises between $10^6$ and $10^8$ cfu of the probiotic per gram of the synthetic nutritional composition.

17. The method of claim 6 wherein the synthetic nutritional composition comprises between $10^5$ and $10^6$ cfu of the probiotic per gram of the synthetic nutritional composition.

* * * * *